United States Patent [19]

Smith

[11] 4,253,450

[45] Mar. 3, 1981

[54] PLASTER OF PARIS BANDAGES WITH CONTROLLED PROPERTIES FROM SYNERGISTICALLY SET-DELAYED AQUEOUS SLURRIES

[76] Inventor: David F. Smith, 101 Briny Ave., Ste. 607, Pompano Beach, Fla. 33062

[21] Appl. No.: 953,925

[22] Filed: Oct. 23, 1978

[51] Int. Cl.³ .................... A61F 13/04; C04B 11/14
[52] U.S. Cl. ................................ 128/91 R; 106/111; 106/112; 106/113; 106/114; 428/255; 428/260
[58] Field of Search ............... 106/110, 111, 112, 113, 106/114, 115, 315; 128/82, 91 R; 428/255, 260

[56] References Cited

U.S. PATENT DOCUMENTS

| | | | |
|---|---|---|---|
| 2,557,083 | 6/1951 | Eberl | 106/110 |
| 3,191,597 | 6/1965 | Smith | 106/115 |
| 3,282,265 | 11/1966 | Smith | 106/115 |
| 3,294,087 | 12/1966 | Smith | 106/110 |
| 3,316,901 | 5/1967 | Smith | 106/115 |
| 3,523,805 | 8/1970 | Smith | 106/115 |
| 3,523,806 | 8/1970 | Smith | 106/115 |
| 3,932,190 | 1/1976 | Smith | 106/111 |

Primary Examiner—James J. Bell

[57] ABSTRACT

Plaster of Paris bandages with controlled set, wettability and bonding are made from aqueous slurries exhibiting synergism in set-inhibition between solutions of ammonia, dextrin and casein.

7 Claims, No Drawings

PLASTER OF PARIS BANDAGES WITH CONTROLLED PROPERTIES FROM SYNERGISTICALLY SET-DELAYED AQUEOUS SLURRIES

Prior art discloses the very low concentrations of ammonium borate or ammonium caseinate can largely delay the set of plaster of Paris (POP) in aqueous solutions (see U.S. Pat. Nos. 2,557,083 by Eberl and 3,191,597 by Smith). Smith has also shown that there is synergism in set-inhibition between high concentrations of ammonia and (1) ammonium borate (U.S. Pat. No. 3,294,087) (2) ammonium caseinate (U.S. Pat. No. 3,282,265) (3) soluble dextrin (U.S. Pat. No. 3,523,806) and (4) soluble, hydrolyzed, polymerized polyvinyl acetate (U.S. Pat. No. 3,932,190; col. 4, lines 7-12). Such methods of set-delay permit POP bandages to be made by forming a slurry of POP in such aqueous solutions, coating a backing material with the slurry and then heating and drying the coated backing to drive off water and ammonia and leave a final, dry product whose set is not delayed. I have now discovered that synergism in set-delay exists between ammonium caseinate, soluble dextrin and moderate concentrations of ammonia; thus saving large amounts of ammonia, and obtaining a desired set-delay with less ammonium caseinate than is required using it alone. It is desirable to be able to use low concentrations of caseinate since upon heating and hydrolysis there is always a small residuum of the caseinate in the finished product that, even in trace amounts, can delay the set a matter of minutes which is important in a bandage whose desired set is 2 to 8 minutes. As a matter of fact, since this residuum is proportional to the original total caseinate used, other factors being equal, we may control the final set by the original amount used, but need to use a low concentration in order to obtain a very fast setting bandage. However, if we use ammonium borate or caseinate alone with only a small excess of ammonia, we have to use so much borate or caseinate as to require excessive drying (slow drying) in order to get a small enough residuum to obtain fast setting.

The accompanying Table I shows the results of typical experiments wherein the data have been calculated to the common basis of 1800 lbs. POP and about 1029 lbs. water (not including the water in the NH$_3$.Aq or aqua ammonia which is the commercial 29.4% NH$_3$). The H$_3$BO$_3$ and casein are in grams; the dextrin, starch, PvAlc and K$_2$SO$_4$ in percent by weight of the 1800 lbs. POP and the NH$_3$.Aq is in pounds of 29.4% aqueous NH$_3$. The pot-life is the time the POP is in the solution before it starts to set. The amount of POP relative to solution is not critical-350 grams POP per 200 grams of free water in the solution forms a slurry that is moderately thick and of a consistency suitable for knife-coating, this being the equivalent of 1029 lbs. water per 1800 lbs. POP. The variation in the K$_2$SO$_4$ concentration in the Table is not critical and affects only the set of the final, dry POP—it can vary from 0.5 to 2.5% of the weight of POP. The PvAlc is a 99.7% hydrolyzed polyvinyl acetate, whose viscosity in 4 weight-percent aqueous solution at 20° C. is 55-65 cps. as determined by a Brookfield Viscometer, Model LVF, using #1 spindle at 60 R.P.M. Other water-dispersible polyvinyl alcohols can be used. All experiments were performed using steam-calcined POP (see Randel and Dailey, U.S. Pat. No. 1,901,051) of particle-size 99% through 200 mesh standard screen as required by the below cited Federal specification, although other types of POP can be used. Although all experiments were made using the same batch of POP, there can be minor differences, for example, there may be slight differences in the contents of Terra Alba (active gypsum) that affect pot-life. Terra Alba is made of slow hydration of POP and can be highly active. The Table contains 2 instances of increased pot-life when the solution is aged—for example stands overnight. This can be due to dissolving of a small amount of slow-dissolving material, somewhat different solution temperature or slight hydrolysis of starch or dextrin. These differences are not sufficient to alter our general conclusions. The starch was cooked at about 12% concentration in water at atmospheric pressure for 1½ hr. It does not appreciably delay the set. The dextrin and PvAlc were dissolved in water at 180° to 212° F. for ½ hr.

Present practice is to use about 900 grams casein per batch of 1800 lbs. POP and about 560 lbs. aqua ammonia—with dextrin alone and no casein or boric acid, about 670 lbs. aqua ammonia. Thus my new process saves much ammonia. Bandages made by spreading a POP slurry on a thin, flexible, inert, absorbable backing material and drying at 180°–250° F. using 1% cooked starch plus dextrin and no boric acid or casein set by the method of GG-B-101d Federal Specification of June 2, 1959, in about 2½ minutes. Those containing 339 g. casein in about 5 min. and with 703 g. in about 8 min. The bandages are spread with sufficient slurry to give a dry weight of 180–250 g. per 4 inch by 5 yard bandage, when the backing weighs 8 g. The 1% starch made a good binder that easily met the above Federal Specification for wet plaster-loss, but without dextrin the roll was somewhat slow to wet when immersed in water preparatory to use in making a cast; but the presence of 0.4% dextrin improved the rate of wetting without largely increasing the plaster-loss. With 1.4–1.7% dextrin, the wetting was very fast but the plaster-loss was greater. Thus the set of the final bandage is controlled by the presence and amount of casein and boric acid and the plaster-loss by the proportion of dextrin to starch in the absence of other bonding agents. The casein, of course, forms ammonium caseinate and the boric acid ammonium borate in the presence of ammonia—the respective anions being the effective molecular species. The borate is much less effective in causing delay of the set and appears to interfere with the effectiveness of the caseinate—perhaps due to competition for the ammonia.

Dextrins are made by partial hydrolysis of starch and vary in solubility from 3 to 9% when stirred in water for 1 hour at 25° C. The dextrin used here was about 5% soluble. The more soluble dextrins are somewhat more effective. Bonding agents other than starch can be used. For example, 0.2 to 1% polyvinyl alcohol (90–100% hydrolyzed polyvinyl acetate), 0.5 to 2% water-insoluble but water-wettable dextran, or a water dispersion of water-insoluble polyvinyl acetate with a softening temperature of 180°–250° F. when the drying temperature of the coated backing is in this range. While water-insoluble binders are preferred, easily water dispersible binders such as methyl cellulose, hydroxypropyl methyl cellulose or hydroxyethyl ethyl cellulose can be used.

As a binder cooked starch is used in amount from 0.8–1.6% of the weight of POP combined with dextrin in amount from 0.3–1.8% of the weight of POP, respectively. While boric acid can be used in amount of 200–1500 g. to control the set of the final, dry product (as residual borate) it precipitates with PvAlc. Casein is used in amount from 100–1200 g. to control the set of the dry product. Aqua ammonia is used in amount from 10–300 lbs.—all figures, of course, per 1800 lbs. POP as in the Table. While batch-process operation makes desirable a pot-life of several hours, a continuous process can operate with as short a pot-life as ½ hr., although a longer pot-life is desirable.

Having thus described my invention, what I claim is:

1. A bandage comprising a flexible, inert, porous, thin, dry backing material carrying about 180 to 250 grams per 4 inch by 5 yard bandage, including about 8 gram of backing, of the residue from evaporation to dryness thereon at about 180° to 250° F. of an aqueous slurry comprising the proportions of 1800 lbs. plaster of Paris and about 1029 lbs. water containing the following minor ingredients: (1) an amount of potassium sulfate equal to from 0.5 to 2.5% of the said weight of plaster of Paris (2) between 10 and 300 lbs. aqua ammonia of about 29.4 weight percent $NH_3$ (3) between 0 and 1500 grams boric acid dissolved in said aqua ammonia (4) between 100 and 1200 grams casein dissolved in said aqua ammonia (5) an amount of dextrin equal to from 0.3 to 1.8% of the said weight of plaster of Paris, said dextrin being of a type that is soluble from about 3% to 9% of its weight when stirred for 1 hr. in water at 25° C. and (6) a water-insoluble binding-agent-solid amount from 0.5 to 2% of the said weight of plaster of Paris and selected from at least one of the class consisting of polyvinyl alcohol, a water-dispersion of water-insoluble polyvinyl acetate with a softening-temperature in the range from 180° to 250° F., water-insoluble but water-wettable dextran and cooked starch; when the amounts of the said aqua ammonia, boric acid, casein and dextrin are at about the minima of their said amounts, setting of the plaster of Paris in said slurry is prevented for a minimum of about ½ hr. and when the amounts of the said aqua ammonia, boric acid, casein and dextrin are at about their said maxima, setting of the plaster of Paris in said slurry is prevented for at least 18 hours.

2. The product of claim 1 wherein the said binding-agent is the said amount of said starch cooked with the said amount of dextrin.

3. The product of claim 1 wherein the said binding-agent is replaced by a material in the same amount but selected from the class of water-dispersible binding-agents consisting of methyl cellulose, hydroxypropyl methyl cellulose and hydroxyethyl ethyl cellulose.

4. The product of claim 2 wherein the relative proportions of the said starch and dextrin are such, within the said limits, as to determine the rate of wetting and the degree of bonding of the final bandage, such proportions being selected from those consisting of (1) the said higher limit of the percent of dextrin combined with the said lower limit of the percent of starch, in order to yield the most rapid wetting bandage and the weakest bonding upon immersing in water the final, dry bandage preparatory to making a cast (2) the said lower limit of the percent of dextrin combined with the said higher limit of the percent of starch in order to yield the slowest rate of wetting and the strongest bonding and (3) intermediate proportions in order to yield intermediate rates of wetting and degrees of bonding.

5. The product of claim 2 selected from the class of those consisting of (1) a minimum sum of the said amounts of casein plus boric acid to yield the fastest-setting final, dry bandage as it is wet for use (2) a maximum sum of the said amounts of casein plus boric acid to yield the slowest-setting final, dry bandages it is wet for use in making a cast and (3) intermediate such sums to yield final, dry bandages of intermediate setting-times as they are wet for use in making casts.

6. The bandage of claim 1 wherein the amounts of the said casein, boric acid, ammonia and dextrin such as used are the respective said maxima so that the plaster of Paris in said slurry is prevented from setting for up to at least 30 hours.

7. The bandage of claim 1 wherein the said evaporation of said slurry is carried out at a rate and at a temperature while moisture is still incompletely evaporated, so as to control the degree of hydrolysis of the therein contained ammonium caseinate and ammonium borate, leaving such unhydrolyzed amounts of caseinate and borate as to slow the set of the final, dry bandage as desired beyond the minimum corresponding to that where there is essentially complete hydrolysis.

* * * * *